US00PP33806P2

(12) United States Plant Patent
Gass

(10) Patent No.: US PP33,806 P2
(45) Date of Patent: Jan. 4, 2022

(54) ***LEUCOPHYLLUM* PLANT NAMED 'MSWNRASCON'**

(50) Latin Name: ***Leucophyllum* x *hybrida***
Varietal Denomination: MSWNRascon

(71) Applicant: Camelot Nurseries Inc., Glendale, AZ (US)

(72) Inventor: Ronald E. Gass, Glendale, AZ (US)

(73) Assignee: Camelot Nurseries Inc., Glendale, AZ (US)

( * ) Notice: Subject to any disclaimer, the term of this patent is extended or adjusted under 35 U.S.C. 154(b) by 0 days.

(21) Appl. No.: 17/219,405

(22) Filed: Mar. 31, 2021

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — C. Anne Whealy

(57) ABSTRACT

A new and distinct cultivar of *Leucophyllum* plant named 'MSWNRascon', characterized by its upright to outwardly spreading plant habit; moderately vigorous growth habit and moderate growth rate; relatively short internodes; freely branching habit; obovate to spatulate-shaped leaves covered with dense silvery pubescence; freely flowering habit with flowers densely clustered; relatively large bright purple-colored flowers; and good garden performance.

2 Drawing Sheets

Figure 1:
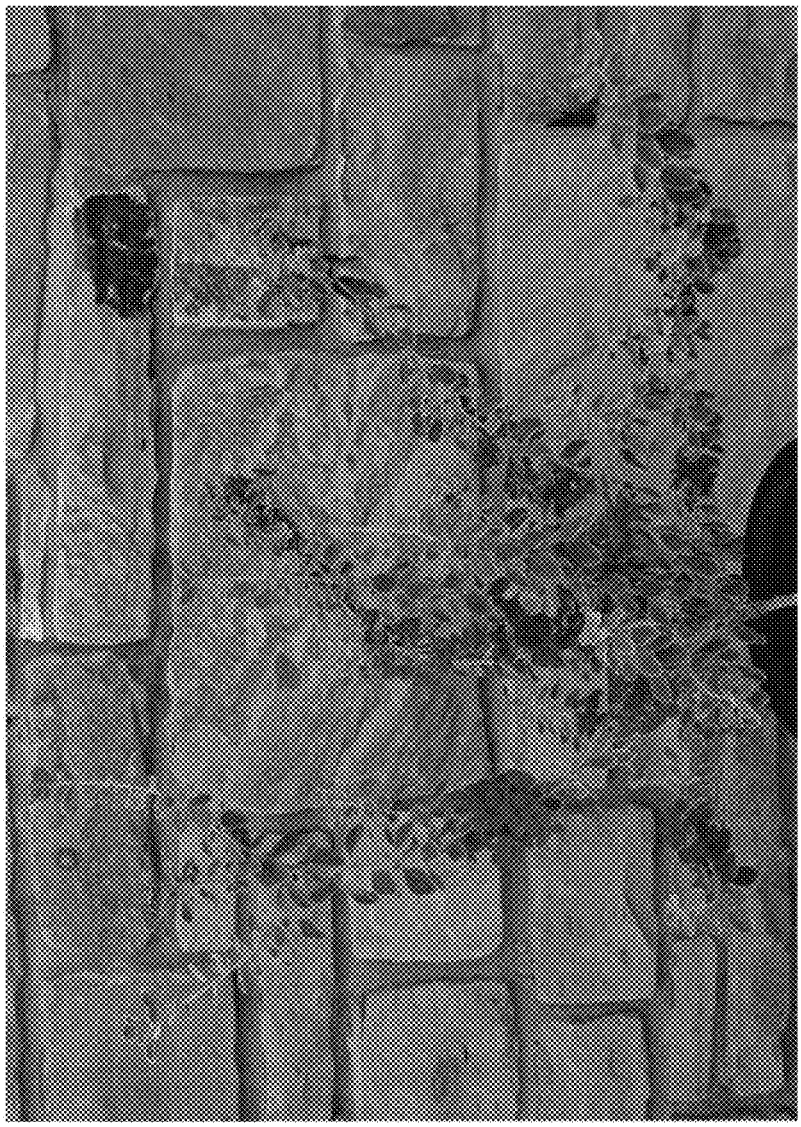

Botanical designation: *Leucophyllum* x *hybrida*.
Cultivar denomination: 'MSWNRascon'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Leucophyllum* plant, botanically known as *Leucophyllum* x *hybrida* and hereinafter referred to by the name 'MSWNRascon'.

The new *Leucophyllum* plant is a product of a planned breeding program conducted by the Inventor in Cochise, Ariz. The objective of the breeding program is to create new uniform and freely flowering *Leucophyllum* plants with attractive flower coloration.

The new *Leucophyllum* plant originated from an open-pollination in July, 2011, in Cochise, Ariz. of *Leucophyllum* x *hybrida* 'Convent', not patented, as the female, or seed, parent with an unknown selection of *Leucophyllum* x *hybrida* as the male, or pollen, parent. The new *Leucophyllum* plant was discovered and selected by the Inventor as a single flowering plant from within the progeny of the stated open-pollination in a controlled environment in Cochise, Ariz. in July, 2012.

Asexual reproduction of the new *Leucophyllum* plant by terminal vegetative cuttings in a controlled environment in Glendale, Ariz. since Sep. 20, 2018, has shown that the unique features of this new *Leucophyllum* plant are stable and reproduced true to type in successive generations.

SUMMARY OF THE INVENTION

Plants of the new *Leucophyllum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MSWNRascon'. These characteristics in combination distinguish 'MSWNRascon' as a new and distinct *Leucophyllum* plant:

1. Upright to outwardly spreading plant habit.
2. Moderately vigorous growth habit and moderate growth rate.
3. Relatively short internodes.
4. Freely branching habit.
5. Obovate to spatulate-shaped leaves covered with dense silvery pubescence.
6. Freely flowering habit with flowers densely clustered.
7. Relatively large bright purple-colored flowers.
8. Good garden performance.

Plants of the new *Leucophyllum* differ primarily from plants of the female parent, 'Convent' in the following characteristics:

1. Plants of the new *Leucophyllum* are more compact and denser than plants of 'Convent'.
2. Flowers of plants of the new *Leucophyllum* are more densely clustered than flowers of plants of 'Convent'.

3. Flowers of plants of the new *Leucophyllum* are purple in color whereas flowers of plants of 'Convent' are magenta in color.

Plants of the new *Leucophyllum* can be compared to plants of *Leucophyllum frutescens* 'Green Cloud', not patented. In side-by-side comparisons, plants of the new *Leucophyllum* differ primarily from plants of 'Green Cloud' in the following characteristics:

1. Plants of the new *Leucophyllum* are more compact and denser than plants of 'Green Cloud'.
2. Flowers of plants of the new *Leucophyllum* are more densely clustered than flowers of plants of 'Green Cloud'.
3. Leaves of plants of the new *Leucophyllum* are silvery in color whereas leaves of plants of 'Green Cloud' are green in color.
4. Flowers of plants of the new *Leucophyllum* are purple in color whereas flowers of plants of 'Green Cloud' are pink in color.

Plants of the new *Leucophyllum* can also be compared to plants of an unnamed selection of *Leucophyllum laevigatum*, not patented, commercially referred to as Chichahuan Sage. In side-by-side comparisons, plants of the new *Leucophyllum* differ primarily from plants of the unnamed selection of *Leucophyllum laevigatum* in the following characteristics:

1. Plants of the new *Leucophyllum* are more compact, denser and more uniform than plants of the unnamed selection of *Leucophyllum laevigatum*.
2. Flowers of plants of the new *Leucophyllum* are more densely clustered than flowers of plants of the unnamed selection of *Leucophyllum laevigatum*.
3. Leaves of plants of the new *Leucophyllum* are silvery in color whereas leaves of plants of the unnamed selection of *Leucophyllum laevigatum* are light green in color.
4. Flowers of plants of the new *Leucophyllum* are purple in color whereas flowers of plants of the unnamed selection of *Leucophyllum laevigatum* are light lavender in color.

BRIEF DESCRIPTION OF THE PHOTOGRAPHS

The accompanying colored photographs illustrate the overall appearance of the new *Leucophyllum* plant showing the colors as true as it is reasonably possible to obtain in colored reproductions of this type. Colors in the photographs may differ slightly from the color values cited in the detailed botanical description which accurately describe the colors of the new *Leucophyllum* plant.

The photograph on the first sheet (FIG. 1) is a side perspective view of a typical flowering plant of 'MSWN-Rascon' grown in a container.

Figure 2:
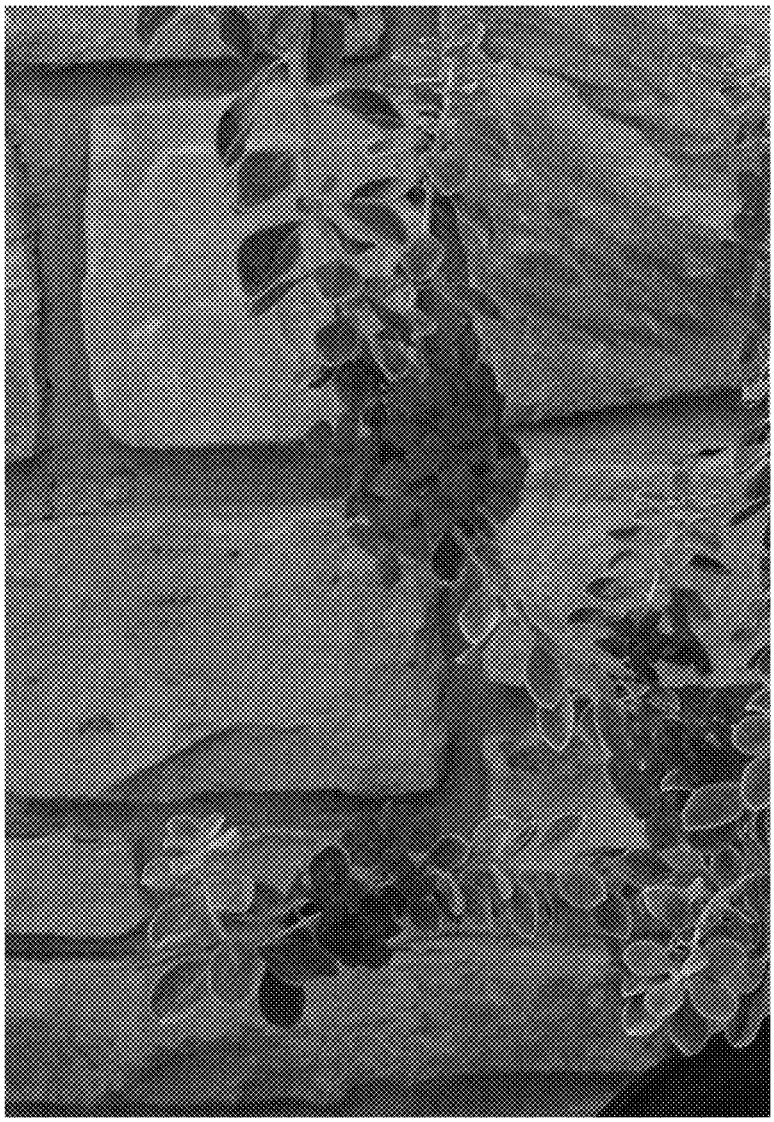

The photograph on the second sheet (FIG. 2) is a close-up view of a typical flowering plant of 'MSWNRascon'.

DETAILED BOTANICAL DESCRIPTION

The aforementioned photographs and following observations and measurements describe plants grown during the spring and summer in one-gallon containers in outdoor nurseries in Glendale, Ariz. and Fort Worth, Tex. and under cultural practices typical of commercial *Leucophyllum* production. During the production of the plants, day temperatures ranged from 10° C. to 47.8° C. and night temperatures ranged from 1° C. to 32.2° C. Plants were two years old when the photographs and description were taken. In the following description, color references are made to The Royal Horticultural Society Colour Chart, 2015 Edition, except where general terms of ordinary dictionary significance are used.

Botanical classification: *Leucophyllum* x *hybrida* 'MSWN-Rascon'.

Parentage:

*Female, or seed, parent.*—*Leucophyllum* x *hybrida* 'Convent', not patented.

*Male, or pollen, parent.*—Unknown selection of *Leucophyllum* x *hybrida*, not patented.

Propagation:

*Type.*—By terminal vegetative cuttings.

*Time to initiate roots, summer.*—About 15 days at soil temperatures about 27° C.

*Time to initiate roots, winter.*—About 30 days at soil temperatures about 22° C.

*Time to produce a rooted young plant, summer.*—About 75 days at soil temperatures about 27° C.

*Time to produce a rooted young plant, winter.*—About 120 days at soil temperatures about 22° C.

*Root description.*—Medium in thickness, fibrous; typically white to light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Perennial shrub; upright to outwardly spreading plant habit; moderately vigorous growth habit and moderate growth rate; freely branching habit with lateral branches potentially developing at every node; relatively dense appearance.

*Plant height.*—About 49 cm.

*Plant diameter.*—About 47 cm.

Lateral branch description:

*Length.*—About 42 cm.

*Diameter, proximally.*—About 5.5 mm.

*Internode length.*—About 1.25 cm.

*Strength.*—Strong; flexible when developing.

*Aspect.*—Primary stems, mostly upright; lateral branches about 45° to 55° from primary stein axis.

*Texture and luster.*—Densely pubescent, lanate; matte; older stems, woody.

*Color, developing.*—Close to 143A; pubescence, close to 193A.

*Color, developed.*—Close to 143A; pubescence, close to 193A to 193B; when woody, close to 199B to 199C without pubescence.

Leaf description:

*Arrangement.*—Alternate, simple.

*Length.*—About 2.3 cm.

*Width.*—About 1.4 cm.

*Shape.*—Obovate to spatulate.

*Apex.*—Obtuse to acute.

*Base.*—Cuneate to attenuate.

*Margin.*—Entire, not undulate.

*Texture and luster, upper and lower surfaces.*—Densely pubescent, lanate; matte.

*Venation pattern.*—Pinnate.

*Color.*—Developing leaves, upper surface: Close to 191A. Developing leaves, lower surface: Close to 191B. Fully expanded leaves, upper surface: Slightly darker than 191A; venation, slightly darker than 191A. Fully expanded leaves, lower surface: Slightly lighter than 191A; midvein, close to 193A to 193B; lateral venation, slightly lighter than 191A.

*Petioles.*—Length: About 3 mm to 4 mm. Diameter: About 1 mm. Strength: Strong, flexible. Texture and luster: Densely pubescent, lanate; matte. Color, upper surface: Close to 191A. Color, lower surface: Close to between 192A and 193A.

Flower description:

*Flower arrangement and habit.*—Single salverform flowers with five fused petals; flowers axillary and densely clustered; flowers face mostly outwardly; freely flowering habit with single flowers potentially developing at every axil during the flowering season.

*Fragrance.*—None detected.

*Natural flowering season.*—Plants flower continuously in the mid to late summer and early autumn in northern Texas.

*Flower longevity.*—Flowers last about two to three days on the plant; flowers not persistent.

*Flower size.*—About 2.2 cm.

*Flower depth.*—About 1.9 cm.

*Flower throat diameter.*—About 5 mm.

*Flower tube length.*—About 1.6 cm.

*Flower tube diameter, proximally.*—About 2 mm.

*Flower buds.*—Length: About 7 mm. Diameter: About 4.5 mm. Shape: Obovate. Texture and luster: Petals, smooth, glabrous and matte; sepals, densely pubescent and matte. Color: Close to 144A; pubescence, close to 193A to 193B.

*Petals.*—Arrangement: Five fused petals in a single whorl; petal lobes are roughly horizontal to the flower tube; petal lobes reflexing with development. Petal lobe length: About 1 cm. Petal lobe width: About 7.5 mm. Petal lobe shape: Spatulate with praemorse apex. Petal lobe margin: Entire; slightly undulate. Petal lobe texture and luster, upper and lower surfaces: Smooth, glabrous; slightly rugose; matte. Throat, texture and luster: Proximally, smooth, glabrous and distally, fine pubescence; matte. Tube, texture and luster: Smooth, glabrous; matte. Color, petal lobes: When opening, upper surface: Close to 77A. When opening, lower surface: Close to 77B. Fully opened, upper surface: Close to 77B; venation, close to 77B; color becoming closer to 77A with development. Fully opened, lower surface: Close to 77B to 77C; venation, close to 77B to 77C; color does not change with development. Color, throat: Distally, close to 77B fading proximally to close to NN155D with spots, close to 163A; venation, similar to lamina colors. Color, tube: Close to NN155D; spots from upper surface are visible; venation, similar to lamina colors.

*Sepals.*—Arrangement: Campanulate calyx with five to six sepals in a single whorl fused at the base. Calyx length: About 5 mm. Calyx diameter: About 3 mm. Sepal length: About 5 mm. Sepal width, free part: About 1.5 mm. Shape: Lanceolate. Apex: Acuminate. Margin: Entire. Texture and luster, upper surface: Smooth, glabrous; slightly glossy. Texture and luster, lower surface: Densely pubescent; matte. Color: When opening and fully opened, upper surface: Close to 144A. When opening and fully opened, lower surface: Close to 144A; pubescence, close to between 193A to 193B and 194A to 194B.

*Peduncles.*—Length: About 2 mm to 2.5 mm. Diameter: About 1 mm. Angle: About 45° to 55° from stein axis. Strength: Strong, flexible. Texture and luster: Densely pubescent; matte. Color: Close to between 193A and 194A.

*Reproductive organs.*—Stamens: Quantity: Four to five per flower. Filament length: About 1 cm. Filament color: Close to NN155D. Anther size: About 1.5 mm by 1 mm. Anther shape: Oblong. Anther color: Close to 161A. Pollen amount: None observed. Pistils: Quantity: One per flower. Pistil length: About 1.5 cm. Style length: About 1.2 cm. Style color: Close to NN155D variably tinged with close to 70A. Stigma diameter: About 1 mm. Stigma shape: Rounded. Stigma color: Close to 70A. Ovary color: Distally, close to 70A and proximally, close to 144A.

*Seeds and fruits.*—To date, seed and fruit development have not been observed on plants of the new *Leucophyllum.*

Pathogen resistance: To date, plants of the new *Leucophyllum* have not been observed to be resistant to pathogens common to *Leucanthemum* plants.

Garden performance: Plants of the new *Leucophyllum* have been observed to have good garden performance, to tolerate drought, arid conditions and temperatures ranging from −12.2° C. to 47.8° C.

It is claimed:

1. A new and distinct *Leucophyllum* plant named 'MSWNRascon' as illustrated and described.

* * * * *